(12) United States Patent
Drevik et al.

(10) Patent No.: US 7,589,250 B2
(45) Date of Patent: *Sep. 15, 2009

(54) ABSORBENT ARTICLE AND METHOD OF PRODUCTION OF AN ABSORBENT ARTICLE

(75) Inventors: Solgun Drevik, Mölnlycke (SE); Anette Gustavsson, Västra Frölunda (SE); Pontus Winqvist, Stora Höga (SE)

(73) Assignee: SCA Hygiene Products AB, Gothenburg (SE)

( * ) Notice: Subject to any disclaimer, the term of this patent is extended or adjusted under 35 U.S.C. 154(b) by 146 days.

This patent is subject to a terminal disclaimer.

(21) Appl. No.: 10/498,562

(22) PCT Filed: Dec. 9, 2002

(86) PCT No.: PCT/SE02/02259

§ 371 (c)(1),
(2), (4) Date: Dec. 23, 2004

(87) PCT Pub. No.: WO03/051250

PCT Pub. Date: Jun. 26, 2003

(65) Prior Publication Data

US 2006/0122569 A1    Jun. 8, 2006

(30) Foreign Application Priority Data

Dec. 18, 2001  (SE)  .................... 0104268

(51) Int. Cl.
*A61F 13/15*  (2006.01)
(52) U.S. Cl. ........................ 604/378; 604/379; 604/380; 604/381
(58) Field of Classification Search ................ 604/378, 604/379, 380, 381, 383
See application file for complete search history.

(56) References Cited

U.S. PATENT DOCUMENTS 3,403,681 A    10/1968   Hoey et al.

(Continued)

FOREIGN PATENT DOCUMENTS

DE    37 05 244    9/1988

(Continued)

OTHER PUBLICATIONS

Summary dated Nov. 7, 2007 of Office Action issued in corresponding Colombia application.

(Continued)

*Primary Examiner*—Jacqueline F. Stephens
(74) *Attorney, Agent, or Firm*—Buchanan Ingersoll & Rooney PC

(57) ABSTRACT

An absorbent article having a first essentially liquid permeable surface layer (13), a backing layer (14) and, located between said liquid permeable surface layer (13) and said liquid impermeable backing layer (14), an absorbent body (15). The absorbent body has cavities (20) which are essentially cone-shaped and extend at least through part of the absorbent body (15), said cavities (20) having a tip part (21) and a base (22), the tip part (21) being located towards or in the liquid permeable surface layer (13) and the base (22) being located away from the liquid permeable surface layer (13). The inner surface of said cavities (20) is treated with at least one functional substance.

12 Claims, 4 Drawing Sheets

U.S. PATENT DOCUMENTS

| | | | |
|---|---|---|---|
| 3,886,941 A | | 6/1975 | Duane et al. |
| 3,929,135 A | * | 12/1975 | Thompson ............. 604/385.08 |
| 3,989,867 A | | 11/1976 | Sisson |
| 3,993,820 A | * | 11/1976 | Repke ......................... 428/167 |
| 4,055,180 A | * | 10/1977 | Karami ....................... 604/368 |
| 4,323,069 A | * | 4/1982 | Ahr et al. .................... 604/378 |
| 4,341,217 A | | 7/1982 | Ferguson et al. |
| 4,435,178 A | * | 3/1984 | Fitzgerald ................... 604/365 |
| 4,681,793 A | | 7/1987 | Linman et al. |
| 4,701,237 A | | 10/1987 | Lassen |
| 4,781,710 A | * | 11/1988 | Megison et al. ............. 604/378 |
| 5,437,653 A | * | 8/1995 | Gilman et al. ............... 604/378 |
| 5,514,120 A | * | 5/1996 | Johnston et al. ............. 604/378 |
| 5,614,283 A | | 3/1997 | Potnis et al. |
| 5,873,963 A | | 2/1999 | Trombetta et al. |
| 5,931,827 A | * | 8/1999 | Buell et al. ............. 604/385.29 |
| 6,110,479 A | | 8/2000 | Blaney et al. |
| 6,153,209 A | | 11/2000 | Vega et al. |
| 6,187,990 B1 | * | 2/2001 | Runeman et al. ............ 604/360 |
| 6,238,379 B1 | | 5/2001 | Keuhn, Jr. et al. |

FOREIGN PATENT DOCUMENTS

| | | |
|---|---|---|
| EP | 0 518 340 A1 | 12/1992 |
| EP | 0 391 108 B1 | 1/1995 |
| EP | 0 875 224 A1 | 11/1998 |
| EP | 1 040 800 A1 | 10/2000 |
| EP | 0 336 578 B1 | 1/2001 |
| JP | 2002-035036 A | 2/2002 |
| SE | 384786 B | 5/1976 |
| WO | WO 96/19173 | 6/1996 |
| WO | WO 96/36757 | 11/1996 |
| WO | WO 99/04739 | 2/1999 |
| WO | WO 99/12734 | 3/1999 |
| WO | 00/10500 A1 | 3/2000 |
| WO | WO 00/56257 | 9/2000 |

OTHER PUBLICATIONS

Notice of Opposition to a European Patent in corresponding Patent No. 02793608.7, dated Apr. 27, 2007, Opponent: The Proctor & Gamble Company.

Notice of Opposition to a European Patent in corresponding Patent No. 02793608.7 dated May 8, 2007, Opponent: Paul Hartman AG, with English Language Summary.

Office Action issued in U.S. Appl. No. 11/251,881 dated Jun. 6, 2006.

Final Office Action issued in U.S. Appl. No. 11/251,881 dated Dec. 5, 2006.

Advisory Action issued in U.S. Appl. No. 11/251,881 dated Mar. 28, 2007.

Office Action issued in U.S. Appl. No. 11/251,881 dated Jul. 3, 2007.

Final Office Action issued in U.S. Appl. No. 11/251,881 dated Feb. 7, 2008.

Advisory Action issued in U.S. Appl. No. 11/251,881 dated May 9, 2008.

Office Action issued in U.S. Appl. No. 11/251,881 dated Aug. 22, 2008.

Notice of Allowance issued in U.S. Appl. No. 11/251,881 dated Mar. 9, 2009.

Office Action issued in U.S. Appl. No. 10/321,538 (now U.S. Patent No. 7,323,615) dated Sep. 21, 2005.

Office Action issued in U.S. Appl. No. 10/321,538 (now U.S. Patent No. 7,323,615) dated Dec. 29, 2005.

Office Action issued in U.S. Appl. No. 10/321,538 (now U.S. Patent No. 7,323,615) dated Jun. 8, 2006.

Notice of Allowance issued in U.S. Appl. No. 10/321,538 (now U.S. Patent No. 7,323,615) dated Sep. 6, 2007.

* cited by examiner

ABSORBENT ARTICLE AND METHOD OF PRODUCTION OF AN ABSORBENT ARTICLE

TECHNICAL FIELD

The invention relates to an absorbent article such as a diaper, a pant diaper, an incontinence pad, a panty liner, a micro panty liner, a sanitary towel or the like, having a first essentially liquid permeable surface layer, a backing layer and, located between said liquid permeable surface layer and said liquid impermeable backing layer, an absorbent body comprising at least one layer.

BACKGROUND ART

When an absorbent article such as a diaper, a pant diaper, an incontinence pad, an incontinence product with a belt, a panty liner, a micro panty liner, a sanitary towel or the like is used, part of the skin is covered in all cases. This means that it is more difficult for the skin to perspire, that is to say to breathe, often with the result that it becomes warm and moist inside the absorbent article. The problem becomes even more marked when the absorbent article has been used, that is to say exposed to motions, urine, menstrual fluid or the like.

Apart from this feeling unpleasant and uncomfortable for the wearer, there are also direct hygienic aspects to be considered. A warm and moist environment is a good breeding ground for bacteria, fungi and the like. This becomes particularly marked in absorbent articles which have been exposed to motions, urine or menstrual fluid (or mixtures thereof), where a warm moist environment together with the bacterial variety which originates from the bodily discharges can lead to active growth of undesirable microorganisms with consequences such as unpleasant odours, skin irritation, rashes, itching and the like.

Attempts to bring about breathability in absorbent articles have previously been made by inter alia using what are known as breathable backings. Document EP 1,040,800 A1, for example, describes a backing layer made of plastic film with perforated holes. However, this document does not offer an adequate solution to the problem as only those parts of the absorbent article which lie next to the backing layer can benefit from the breathable backing and the increased airiness it is said to afford.

Another problem in connection with breathable absorbent articles is that moisture from the skin of the user may condense on the outside of the absorbent article. This may cause the article to be perceived as damp and wet and can be interpreted to mean that liquid has leaked through the article even though the article is, in fact, dry and has much remaining absorption capacity.

For smaller incontinence pads, panty liners or micro panty liners, it is important to fully utilise the volume of the article since it is important that the articles are small, light and conformable. This implies that it is undesirable to add functional substances or properties to the absorption core which may negatively affect the absorption capacity since it is already relatively limited due to the small size of the article.

Further, it is a problem in a purely production related sense to add functional substances without losing too much in production properties such as production speed.

A need therefore exists not only to create a fully breathable absorbent article, which can transport moist air away from generally the whole of the absorbent article, but also to handle the moisture that is transported out from the absorbent article. A need also exists for creating an administering means for adding functional substances to the absorbent article and for solving or alleviating the just mentioned problems.

DISCLOSURE OF INVENTION

By means of the present invention, an absorbent article of the type referred to in the introduction has been produced, which article essentially eliminates the problems of previously known such articles. An article made according to the invention is characterized mainly in that the absorbent body has cavities which are essentially cone-shaped and extend at least through part of the absorbent body, and in that said cavities have a tip part and a base, the tip part being located towards or in the liquid permeable surface layer and the base being located away from the liquid permeable surface layer and that an inner surface of said cavities is treated with at least one functional substance.

In one embodiment of the invention, said backing layer at least partially forms generally cone-shaped cavities in the absorbent body, the backing layer then being treated with at least one functional substance.

In accordance with the invention, the interior of the absorbent body is exposed, and not only its outer surfaces, by means of the backing layer being actively formed to reach into at least a part of the absorbent body.

The backing layer can be treated with at least one functional substance. By a functional substance is meant a substance which brings an additional function to the absorbent body or the backing layer, i.e. a function which the absorbent body and the backing layer would be lacking without the functional substance.

The backing layer can also act as a stiffening element for the absorbent article. This is advantageous in order to prevent the cavities from collapsing when the absorbent article is being used.

Below, the expression "essentially cone-shaped cavities" is used but it is obvious that the expression essentially cone-shaped cavity can be exchanged for pyramid-like or funnel-like shape or intermediate shapes within the scope of the invention. The shape of the tip of an ordinary screwdriver or a Phillips® screwdriver are also intended to be included in the definition of an essentially cone-shaped cavity.

Hence, by essentially cone-shaped cavities are meant not only purely conical cavities but also cavities having more sides than a pyramidal shape (a pyramidal shape has a base with three or four sides). It is pointed out that the more sides the essentially cone-shaped cavity has, the closer it comes to a pure cone shape. Thus, in line with the invention, this implies that all generally cone-shaped cavities having bases with more than three sides are to be regarded to fall within the definition.

Thus, in one embodiment, the envelope surface of the essentially cone-shaped cavities is completely or partially formed by the backing layer. The envelope surface will then have the surface properties of the backing layer, which is very advantageous. For instance, by using a hydrophobic backing layer, it is possible to achieve a hydrophobic envelope surface area aiding the essentially cone-shaped cavities in not letting through hydrophilic liquid such as, for instance, urine.

By making essentially cone-shaped cavities through at least part of the absorbent body, an airy absorbent article is produced without appreciably impairing the leakage security. The absorption capacity in the ventilated absorbent body can even be regenerated to a certain extent by virtue of the liquid drying out. The precondition for this form of regeneration of the absorption capacity is that the absorbent article is very airy, that is to say breathable, because it should dry out as quickly as possible.

The liquid which the wearer discharges when wearing the article will not run down into the essentially cone-shaped cavities on account of the capillary forces in the tips of the cavities. As the cavities are essentially cone-shaped, the liquid will initially tend to remain in the tip of the cone, thereafter being absorbed by the absorbent body and thus not running through the article. The effect of capillary forces in connection with absorption is well documented and does not have to be explained further.

The treatment of the inner side of the essentially cone-shaped cavities or the backing layer in order to provide the absorbent body with further or improved properties works because the essentially cone-shaped cavities extend into at least a portion of the absorbent body, thus exposing the interior of the absorbent body to the functional substances, thereby offering a number of possibilities of creating properties, i.e. function-adding and/or function-boosting properties in the absorbent body by using the inner side of the cavities or the backing layer. This can be done in connection with the formation of the essentially cone-shaped cavities in the absorbent body for instance by treating the roller which makes the holes.

It is possible to modify the properties of the envelope surface in the essentially cone-shaped cavities by treating the backing layer before it is perforated and the essentially cone-shaped cavities are formed. The backing layer can also be treated during the perforation itself, for instance by way of the perforation roller being coated with an agent which is transferred to the backing layer during the perforation. In the latter case, the inner side of the essentially cone-shaped cavity will be partially treated by treatment of the side of the backing layer which is facing away from the absorbent body.

Among a number of possible treatments of the backing layer, pH-treatment for pH-control or treatment in order to obtain a more hydrophobic surface may be mentioned. In some cases, it can be desirable to apply treatment in order to obtain a less hydrophobic surface or a hydrophilic surface. It is also possible to employ an indicator treatment in order to indicate various conditions such as temperature, moisture content, pH, enzymatic activity, or the like. Further, the backing layer can be treated in order to add bacteria in the article. One example of suitable bacteria is lacto-bacteria, but treatment for odour control or a number of other similar functions is possible.

According to one embodiment, the backing layer is treated with a superabsorbent material on the side which in normal use is facing away from the user. Thereby, the inner side of the essentially cone-shaped cavities can collect condensed moisture from the skin of the user. This makes the article feel dry and fresh even during long periods of use. The superabsorbents can easily be attached to the backing layer by means of adhesive. Alternatively, the superabsorbents can be placed within the backing layer, the backing layer in such a case usually consisting of a laminate or similar.

Naturally, it is within the scope of the invention to treat both sides of the backing layer with functional substances as well as only the inner side, i.e. the side of the backing layer which is facing the liquid permeable surface layer, or only the outer side, i.e. the side of the backing layer which is facing away from the liquid permeable surface layer.

BRIEF DESCRIPTION OF DRAWINGS

The invention will be described in greater detail below with reference to figures shown in the accompanying drawings, in which.

DESCRIPTION OF EMBODIMENTS

Figure 1:
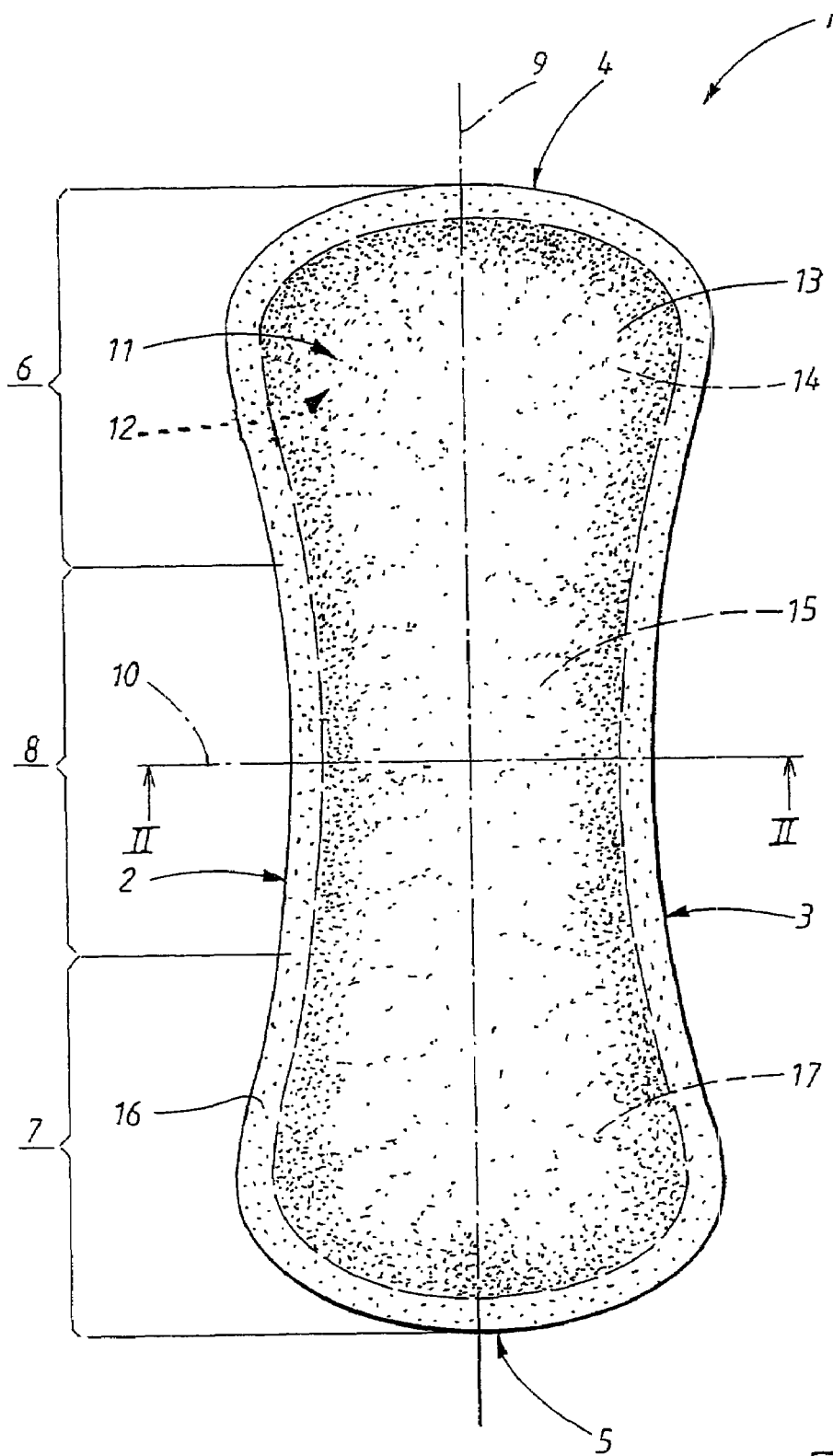
FIG. 1 shows a panty liner.

The invention can be applied to a number of different absorbent articles, for example diapers, pant diapers, incontinence pads, incontinence products with a belt, panty liners, micro panty liners, sanitary towels or the like. However, only a panty liner will be described below.

The panty liner 1 in FIGS. 1 and 2a-e has an essentially elongate shape with a longitudinal direction and a transverse direction and has two long sides 2, 3, two short sides 4, 5, a first end portion 6 intended to be facing forward on a user, a second end portion 7 intended to be facing rearward on a user and a crotch portion 8 located between the first end portion 6 and the second end portion 7, a longitudinal centre line 9 extending in the longitudinal direction of the panty liner and a transverse centre line 10 extending in the transverse direction of the panty liner. Centre line means a line which runs in the longitudinal or transverse direction and is located at an equal distance from the long sides 2, 3 or the short sides 4, 5, respectively, of the panty liner 1. The panty liner 1 has a top side 11 which is intended to face the wearer during use and an underside 12 intended to face away from the wearer.

The panty liner 1 comprises a liquid permeable surface layer 13 arranged on the top side 11 so that it faces the wearer during use, and a liquid-barrier backing layer 14 on the underside 12. Arranged between the surface layer 13 and the liquid-barrier backing layer 14 is an absorbent body 15. The surface layer 13 and the liquid-barrier backing layer 14 are suitably connected to the absorbent body 15 by adhesive and, during manufacture of the panty liner, the various layers can be pressed together during adhesive bonding by an embossed roller, for example around the edge 16 of the panty liner. It is also possible to emboss patterns into the article during manufacture. Inside the edge 16, the article is of essentially uniform thickness, which means that it has a planar shape in order to obtain good contact with the outer parts of the genital area of the wearer.

On the underside 12 of the panty liner, there may be fastening means (not shown in the figure) in the form of, for example, pressure-sensitive adhesive. The adhesive can cover the entire underside, be applied in parallel strands along the underside or be applied to the underside in another suitable pattern such as, for example, diamond patterns or dots. A removable protective layer can be arranged over the adhesive. The protective layer is removed by the wearer before fitting the panty liner in the underwear of the wearer. The protective layer can be, for example, what is known as a release paper which can consist of a plastic layer or a paper layer coated with silicone, but can also be made of another material with release characteristics, for example a packing material. It is also possible to use other fastening means, such as hook-and-loop fasteners, for instance VELCRO® or friction fastening.

The surface layer 13 can consist of any conventional material, for example one or more nonwovens, one or more plastic films, perforated non-woven, perforated plastic film, laminates of the materials just mentioned above or combinations thereof. The surface layer can be hydrophobic or hydrophilic or both.

The backing layer 14 can consist of a material such as, for example, a thin plastic film, or of a material which is in itself substantially liquid permeable. Further examples of suitable materials are nonwovens, rayon, cellulose fibres, cotton, liquid permeable plastic films of polyethylene, polyester, polystyrene or polypropylene, foam, nonwovens or laminates of nonwovens and liquid permeable plastic films. It is also possible to provide the backside of the panty liner with a liquid permeable backing layer of, for instance, SMS (spunbond-meltblown-spunbond). It is important that the material in the backing layer 14 be chosen so that it is well adapted to at least one of the functional substances.

In accordance with one embodiment, the backing layer consists of a somewhat more rigid material so that the cavities will not collapse completely during use. However, it is good if the backing layer is flexible and elastic so that the cavities may deform during a shorter period but regain their initial shape when they are no longer exposed to pressure or other forms of stress which may cause deformation. Some examples of materials (as well as certain combinations of materials) which have been found to have sufficient bending stiffness and torsional stiffness to temporarily or permanently resist uncontrolled deformation are described in EP 0 336 578 where also the measuring method ASTM D 4032-82 "Circular bend procedure" is described in detail.

In one embodiment, the backing layer 14 is essentially liquid-impermeable. The backing layer 14 can therefore consist of any material which satisfies the criterion of liquid-impermeability so that leakage from the underside is prevented and which has sufficient flexibility and skin-friendliness for the purpose. A backing layer which consists of a laminate of a liquid impermeable plastic layer facing the absorbent body and a nonwoven facing the undergarment of the wearer provides a leakage secure barrier layer having a textile feel. Further examples of suitable materials are non-woven, rayon, cellulosic fibres, cotton, plastic films made of polyethylene, polyester or polypropylene, foams, nonwovens and laminates of nonwovens and plastic films. In addition, it is possible to provide the backside of the panty liner with a liquid-impermeable backing layer of for instance SMS (spunbond-meltblown-spunbond). It is important that the material in the backing layer 14 be chosen so that it is well adapted to at least one of the functional substances.

The absorbent body 15 is suitably made from natural fibres such as, for example, cellulose pulp, absorbent synthetic fibres or mixtures of natural fibres and synthetic fibres. The absorbent body 15 preferably consists of an airlaid cellulose body. It is also possible to mix what are known as superabsorbents into the absorbent body. The absorbent body 15 can also contain additional components such as shape-stabilizers, liquid-spreading means or binders. It is also possible to use various types of absorbent foamed material in the absorbent body. The absorbent body can of course be constructed from one or more different layers; at least one admission layer, for example, can also be included in the absorbent body. In the following figures, the absorbent body and the admission layer are described separately, but this is only to indicate a number of different embodiments which are possible within the scope of the invention and is not intended to limit the definition of absorbent body to a body without an admission layer.

An admission layer 17 is arranged between the surface layer 13 and the absorbent body 15. The purpose of the admission layer 17 is to draw liquid into the absorbent article, spread the liquid and transport the liquid down to the absorbent body 15. The admission layer 17 can be made of, for example, a low-density non-woven material, wadding, high-loft material or the like.

Figure 2A:
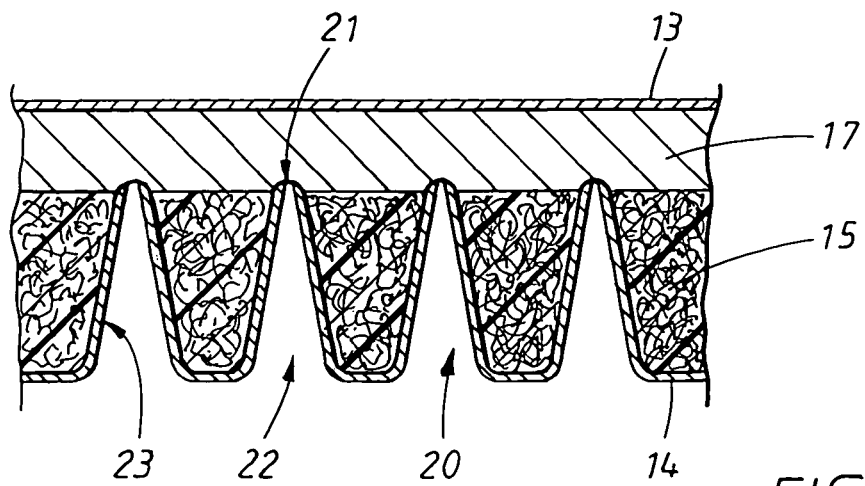
FIG. 2a shows part of a section along the line II-II through the panty liner in FIG. 1.

FIG. 2a shows part of a section through the panty liner in FIG. 1 along the line II-II in FIG. 1. The panty liner also shows the surface layer 13, the liquid-barrier backing layer 14 and also the admission layer 17 and the absorbent body 15. The admission layer 17 is located between the surface layer 13 and the absorbent body 15. The absorbent body 15 is located between the admission layer 17 and the backing layer 14. The panty liner 1 in FIGS. 1 and 2 has essentially cone-shaped cavities 20 which, in this embodiment, extend all the way through the absorbent body 15 and a little way into the admission layer 17. The essentially cone-shaped cavities 20 have a tip 21 and a base 22, the tip 21 having a smaller circumference than the base 22. According to FIGS. 2a-e, the tip is located closer to the surface layer 13 than the base 22. The cone-shaped cavities 20 also each have an inner wall 23 or envelope surface which consists entirely or partly of the backing layer 14 which, during manufacture, helps to form the essentially cone-shaped cavities 20. The inner wall 23 also helps, after manufacture, to keep the shape of the essentially cone-shaped cavities 20. The inner wall 23 of the essentially cone-shaped cavities 20 can also consist entirely or partly of the absorbent body 15 in a manner not shown in the figure.

Figure 2B:
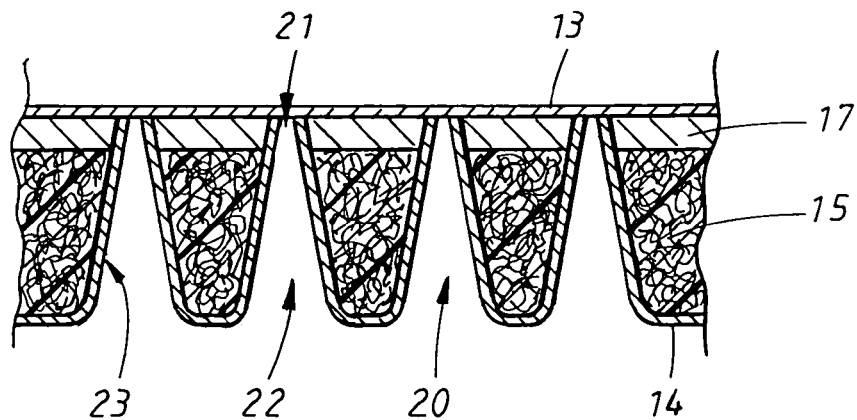
FIG. 2b shows part of a section along the line II-II through the panty liner in FIG. 1 for an alternative embodiment of the invention.

FIG. 2b shows part of a section of another embodiment. The section shows the surface layer 13, the backing layer 14 and also the admission layer 17 and the absorbent body 15. The admission layer 17 is located between the surface layer 13 and the absorbent body 15. The absorbent body 15 is located between the admission layer 17 and the backing layer 14. The panty liner in FIG. 2b has essentially cone-shaped cavities 20 which, in this embodiment, extend all the way through the absorbent body 15 and all the way through the admission layer 17. The essentially cone-shaped cavities 20 have a tip 21 and a base 22, the cavity having a smaller circumference at the tip 21 than at the base 22. In FIG. 2b, the tip 21 is located closer to the surface layer 13 than the base 22. The cone-shaped cavities 20 also each have an inner wall 23 which consists entirely of the backing layer 14.

Figure 2C:
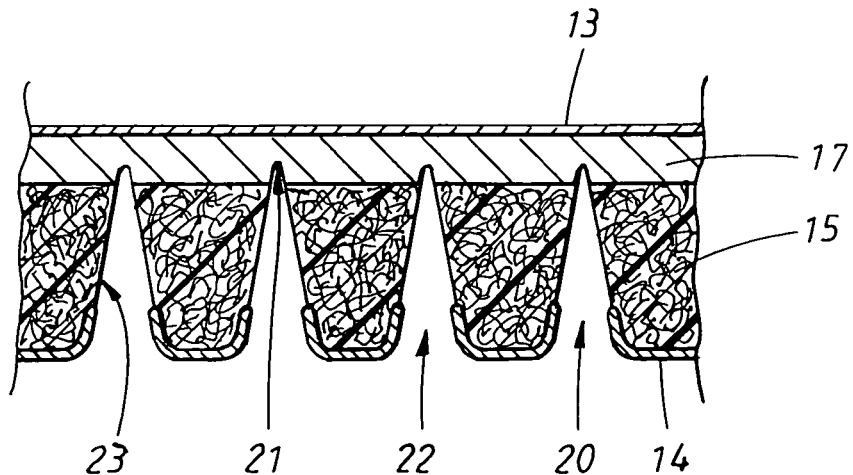
FIG. 2c shows part of a section along the line II-II through the panty liner in FIG. 1 for an alternative embodiment of the invention.

FIG. 2c shows part of a section of a further embodiment of a panty liner. The section shows the surface layer 13, the backing layer 14 and also the admission layer 17 and the absorbent body 15. The admission layer 17 is located between the surface layer 13 and the absorbent body 15. The absorbent body 15 is located between the admission layer 17 and the backing layer 14. The panty liner in FIG. 2c has essentially cone-shaped cavities 20 which, in this embodiment, extend all the way through the absorbent body 15 and part of the way through the admission layer 17. The essentially cone-shaped cavities 20 have a tip 21 and a base 22, the circumference of the cavities being smaller at the tip 21 than at the base 22. The cone-shaped cavities 20 also each have an inner wall 23 or envelope surface which consists partly of the backing layer 14 and also of the absorbent body 15 and to a certain extent the admission layer 17.

Figure 2D:
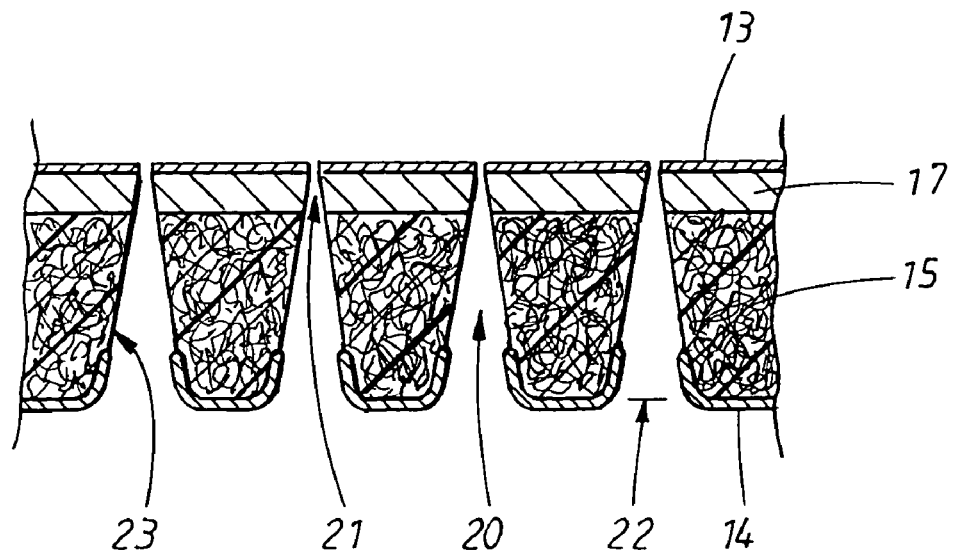
FIG. 2d shows part of a section along the line II-II through the panty liner in FIG. 1 for an alternative embodiment of the invention.

FIG. 2d shows part of a section of a further embodiment of a panty liner. The section shows the surface layer 13, the backing layer 14 and also the admission layer 17 and the absorbent body 15. The admission layer 17 is located between the surface layer 13 and the absorbent body 15. The absorbent body 15 is located between the admission layer 17 and the backing layer 14. The panty liner in FIG. 2d has essentially cone-shaped cavities 20 which, in this embodiment, extend all the way through the absorbent body 15 and all the way through the admission layer 17 and also through the surface layer 13. The essentially cone-shaped cavities 20 have a tip 21 and a base 22, the circumference of the cavities 20 being smaller at the tip 21 than at the base 22. The cone-shaped cavities 20 also each have an inner wall 23 or envelope surface which consists partly of the backing layer 14 and also of the absorbent body 15 and to a certain extent the admission layer 17 and the surface layer 13.

Figure 2E:
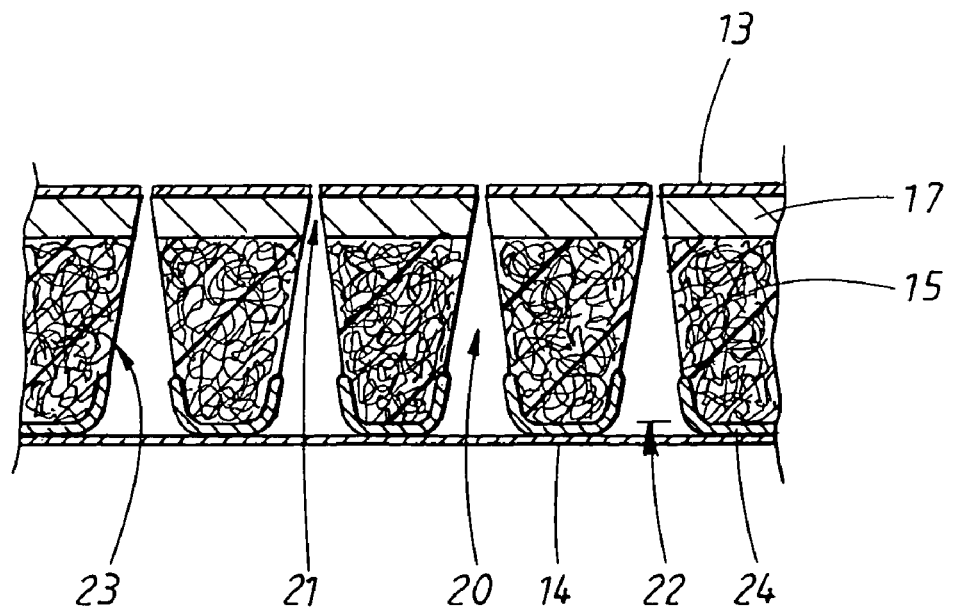
FIG. 2e shows part of a section along the line II-II through the panty liner in FIG. 1 for an alternative embodiment of the invention.
Figure 2F:
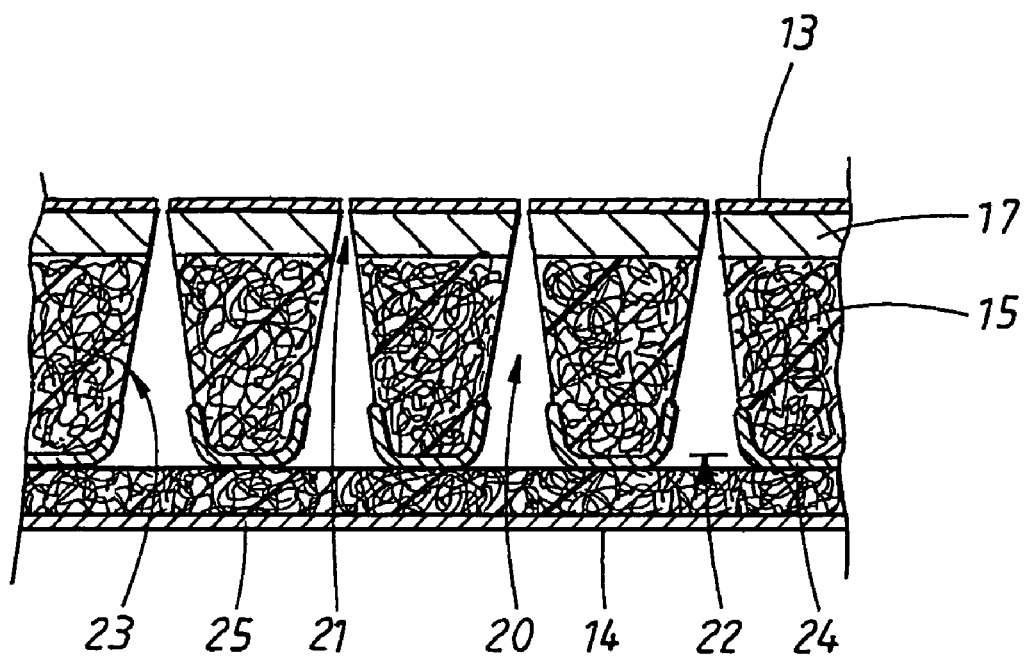
FIG. 2f shows part of a section along the line II-II through the panty liner in FIG. 1 for an alternative embodiment of the invention.

FIG. 2e shows part of a section of a further embodiment of a panty liner. The section shows the surface layer 13, a first backing layer 24 and also the admission layer 17 and the absorbent body 15. The admission layer 17 is located between the surface layer 13 and the absorbent body 15. The absorbent body 15 is located between the admission layer 17 and the first backing layer 24. The panty liner in FIG. 2e also has essentially cone-shaped cavities 20 which, in this embodiment, extend all the way through the absorbent body 15 and all the way through the admission layer 17 and also through the surface layer 13. The essentially cone-shaped cavities 20 have a tip 21 and a base 22, the circumference of the cavities 20 being smaller at the tip 21 than at the base 22. The cone-shaped cavities 20 also each have an inner wall 23 or envelope surface which consists partly of the first backing layer 24 and also of the absorbent body 15 and to a certain extent the admission layer 17 and the surface layer 13. The panty liner in FIG. 2e also has a second, outer backing layer 14 which is located against the first backing layer 24 so that the essentially cone-shaped cavities 20 are not visible, or are not immediately conspicuous. The first backing layer 24 and the second backing layer 14 can consist of the same material but can also consist of different materials. Preferably, at least the second backing layer 14 is made of an essentially breathable material.

Within the scope of the invention, it is also possible to arrange a further absorbent body 25, for instance similar to the existing absorbent body 15, between the first backing layer 24 and the second backing layer 14.

Some Examples of Functional Substances:

The best way to avoid the occurrence of dermatitis is to create conditions counteracting the factors that start and support the diaper dermatitis process. For this reason, the aim should be to keep the skin as dry as possible (something that is made possible for instance with the present invention), to air the skin frequently and to change wet diapers. Mechanical shear forces should be minimised by choosing materials that are as smooth and soft as possible, thereby reducing chafing between the diaper and the skin. Further, it is possible to strengthen the barrier against penetration of irritants and enzymes by adding a softening and protecting lotion or cream to the skin. In more serious cases of dermatitis, micro-organisms may have infected the damaged skin and treatment with more active means will be required. In such instances, ointments with cortisone and various fungicides and bactericides are used. Accordingly, it is advantageous to reduce the amount of aggressive micro-organisms in the absorbent article.

As previously mentioned, the backing layer exposes the absorbent body to the functional substances. Moreover, the substances in accordance with one embodiment of the invention are pressed out of the tip of the cavity when the absorbent article is exposed to pressure, for instance when being sat on. This implies that if, for example, a skin care agent is applied to the inner side of the cavities, it will be pressed out towards the liquid-permeable surface layer through the tip of the cavity and subsequently be transferred to the user.

A skincare agent can be used in order to prevent, alleviate or heal dermatitis. In the manufacturing process, the functional substances can be in the form of a solution, a suspension, a cream, a lotion, a salve, a paste, a gel, a foam, an aerosol, a capsule or in a solid state as particles, flakes, fibres, films, foam, waddings, sticks, etc. In cases where the agent does not attach to the backing layer by itself, it can be suitable to glue it on, for instance with adhesive, for example hot melt adhesive, by laminating or to attach the agent to the backing layer in some other way.

By a Functional Substance is Meant (Separately or in a Mixture):

Lipids (fats, oils, waxes), solvents (including water), water-soluble substances, surface-active agents (emulsifiers, surfactants), viscosity-regulating substances, pH-regulating substances, preserving agents, complexing agents (e.g. chelates), delivery systems (e.g. liposomes, microcapsules, etc), pigments, perfumes, and active substances (also pharmaceutical agents). The lipids are usually emulsified in water, known as o/w emulsion, or water is emulsified in the lipid phase, known as w/o emulsion.

The functional substance can include lipids such as:

paraffins (alkanes) with 12-35 carbon, for example paraffin oil (mineral oil) or petrolatum (vaseline).

Triglycerides, refined and/or hydrogenated, animal or vegetable with preferably carbon chain lengths of under C-18 (e.g. milk fat, coconut oil *Cocous nocifera*, palm-kernel oil *Elaeis guineeis*), animal or vegetable with unsaturated C-18 fatty acids (e.g. Japan wax *Rhus succesdanes*, tallow fat, soybean oil *Glycerin soya*, peanut oil *Arachais hypogaea*, maize oil *Zea mays*, sunflower oil *Helanthus annus*, grapeseed oil *Vitis vinifera*, safflower oil *Carthamus tinctorius*, sweet almond oil *Prunnus amygdalus* dulcis, hazelnut oil *Corylus americana*, walnut oil *Juglans regia*, olive oil *Olea europasa*, avocado oil *Persea gratissima*, sesame oil *Sesamum indicum*, tall oil, Tallol, cottonseed oil Gopssypium, palm oil *Elaesis guineensis*, rice oil *Oryza sativa*, rape oil Canola, apricot-kernel oil *Prunus armeniaca*, cocoa butter *Theobroma cao*, shea butter *Butyrospermum parkii*, wheatseed oil *Triticum vulgare, Bassia latifola*), animal or vegetable with carbon chains over C-18 (e.g. beeswax *Cera alba*, shellac wax Shellac cera, meadowfoam seed oil *Limnanthes alba*, rapeseed oil *Brassica capmestris*, cucumberseed oil *Borago officinalis*, linseed oil *Linum usitatissimum*, ricin oil *Ricinus communis*, veronia oil *Veronia galamensis*, jojoba oil *Buxus chinensis*, candlewax *Euphorbia cera*, ongokea oil *Ongokea gore*).

Fatty alcohols with straight or branched carbon chain lengths of 12-32 carbons. For example, cetyl alcohol or stearyl alcohol.

Fatty acid esters with 12-32 carbons. For example, methyl palmitate, methyl stearate, isopropyl myristate, isopropyl laurate, isopropyl palmitate, isopropyl stearate, octyl palmitate, octyl stearate or octyl laurate.

Polyalcohols. For example, sugar alcohols or polyglycerols.

Complex lipids. For example, phospholipids or sphingolipids (ceramides).

Waxes. Of animal origin, for example beeswax or lanolin. Of vegetable origin, for example carnauba or candelilla. Of mineral origin, for example ozocerite or ceresin.

Polysiloxanes. Straight, branched or cyclic. For example, polydimethylsiloxane (dimethicone) or polydiethylsiloxane.

The functional substance can include emulsions such as:
Emulsions of one or more fats with hydrophilic substances such as water, glycerol, polyethylene glycol (PEG), propylene glycol, butylene glycol, sorbitol, silicone glycols or the like or mixtures thereof.

The functional substance can include substances which adsorb irritating components in urine or excrement. For example, clay mineral (bentonite, kaolin, montmorillonite, etc), silicon oxide compounds (quartz, zeolites, water glass, etc) or activated charcoal. The substances can advantageously have been activated to be more adsorbent by means of various treatments, for example with quaternary ammonium compounds.

The functional substance can include enzyme inhibitors. For example, metal salts of iron or zinc, trace amounts of heavy metal ions such as copper or silver, ethylene diamine tetraacetic acid (EDTA), soybean trypsin inhibitor, lima bean protease inhibitor, maize protease inhibitor, stearylglycyrrhetinate, glycerol triacetate, betaine compounds, sulphobetaine compounds, cholestyramine, p-guanidinobenzoates.

The functional substance can include pH-regulating additives. For example, organic or inorganic acids such as adipic acid, ascorbic acid, benzoic acid, citric acid, malic acid, tartaric acid, lactic acid, phosphoric acid or hydrochloric acid. Or buffers made for example from said acids with corresponding salts. Can also include polymeric acids, for example polyphosphoric acid or polyacrylic acid.

The functional substance can also include additions of probiotic microorganisms, characterized by being antagonistic towards undesired microorganisms, e.g. urinary tract pathogens or skin infection pathogens. Examples of probiotic microorganisms which can be used are individual strains or mixtures of several strains of lactic acid bacteria taken from the species *Lactobacillus acidophilus, Lactobacillus curvatus, Lactobacillus plantarum* or *Lactococis lactis*.

The functional substance can also include more or less active substances such as:
Anti-inflammatory agents, e.g. acetylsalicylic acid, allantoin, azulen, alpha-bisabolol (chamomile), flavonoids, glycyrrhizinic acid, ichthammol (Inotyol®)), tannins.
Astringents (vasoconstrictors), for example TiO, ZnO (and other Zn compounds), aluminium acetate solution, aluminium tartrate solution (and other Al compounds), ethanol or ethanol-based solutions.
Aloe vera (Aloe barbadensis), alpha-hydroxy acids (citric acid, tartaric acid, lactic acid, malic acid, etc.), algae extract, ascorbic acid (vitamin C), vitamin A compounds (retinol, retinal, tretinoin and isotretinoin), avocado sterols, betaine (trimethylglycine), ceramides, grapeseed extract, essential fatty acids, flavonoids, phytosphingosine, phytosterols, hyaluronic acid, yeast extract, chitosan, milk protein (Lactis proteinum), pantenol (provitamin B5), polysaccharides, rosemary extract, tocopherol (vitamin E), ubiquinone (coenzyme Q10), urea.
Antimicrobial agents, for example amorolfin, antibiotics, bacitracin, benzalkonium chloride, benzetonium chloride, cetrimide, fusidic acid, gentian violet (methylrosaniline chloride), hexachlorophene, hexylresorcinol, imidazole derivataves (for example biphonazole, econazole, ketoconazole, chlotrimazole, miconazole), chlorhexidine, nystatin, povidone-iodine, terbinafin, triclosan, hydrogen peroxide.
Antiviral agents, for example acyclovir, imiquimod, podophyllotoxin, podophilox, cidofovir, penciclovir, vidarabin, idoxuridine, trifluridine, tromantadine, lamivudine.

The functional substance can also include glucocorticoids, preferably of low potency, for example hydrocortisone, or antipruritic, for example antihistamines or local anaesthetics (e.g. lidocaine).

The functional substance can also consist of ready-made mixtures of skin ointments, creams and lotions. For example, Necesse® Lotion (ingredients: aqua, propylene glycol, liquid paraffin, octyl octanoate, urea, PEG-8 distearate, steareth-2, steareth-21, betaine, lactic acid, tocopheryl acetate, dimethicone, tromethamine, methylparaben, propylparaben, perfume), Necesse® Skin Cream (ingredients: aqua, liquid paraffin, octyl stearate, sodium chloride, urea, glyceryl stearate, stearic acid, cetearyl alcohol, PEG-30 stearate, tocopheryl acetate, tromethamine, dimethicone, methylparaben, sorbic acid, propylparaben, perfume), Necesse® Barrier Cream (ingredients: petrolatum, glycerol, Arachis hypogaea, triethyl citrate, tocopheryl acetate) or Necesse® Zinc Ointment (ingredients: petrolatum, Arachis hypogaea, zinc oxide, retinyl palmitate, tocopherol). Necesse® products are sold commercially by SCA Hygiene Products, Gothenburg, Sweden.

The functional substance may comprise superabsorbents in the form of particles or fibres. A cross-linked polyacrylate can, for instance, be used (one example of such a polyacrylate is disclosed in detail in EP 0 391 108). Further, what is known as acidic superabsorbents may also be included.

The invention claimed is:

1. Absorbent article having a first external essentially liquid permeable surface layer that faces a user when the absorbent article is being worn, a liquid impermeable backing layer and, located between said liquid permeable surface layer and said liquid impermeable backing layer, an absorbent body, wherein the absorbent body has cavities which are essentially cone-shaped and extend at least through part of the absorbent body, and said cavities have a tip part and a base, the tip part being located in the liquid permeable surface layer and the base being located away from the liquid permeable surface layer, and an inner surface of said cavities is treated with at least one functional substance.

2. Article according to claim 1, wherein said liquid impermeable backing layer at least partially forms the essentially cone-shaped cavities.

3. Article according to claim 1, wherein the liquid impermeable backing layer is treated with at least one functional substance.

4. Article according to claim 1, wherein the liquid impermeable backing layer is essentially liquid impermeable.

5. Article according to claim 1, wherein the functional substance is chosen among one or more of: superabsorbents, pH-controlling substances, adhesive, anti-microbial substances, glucocorticoids, antiviral agents, probiotic microorganisms, enzyme inhibitors, lipids, silicone oxide compounds or active substances, for instance antipruritic substances.

6. Article according to claim 1, wherein the article comprises a second backing layer which is essentially liquid impermeable.

7. Article according to claim 6, wherein a further absorbent body is placed between the first and the second backing layer.

8. Article according to claim 1, wherein the functional substance is applied to the side of the liquid impermeable backing layer facing the liquid permeable surface layer.

9. Article according to claim 1, wherein the functional substance is applied to the side of the liquid impermeable backing layer which is facing away from the liquid permeable surface layer.

10. Article according to claim 1, wherein the liquid impermeable backing layer is a laminate.

11. Article according to claim 1, wherein the liquid impermeable backing layer is an external layer.

12. Article according to claim 1, wherein the liquid permeable surface layer is an outermost layer of the absorbent article.

* * * * *